US00PP13899P39

(12) United States Plant Patent
Pieters

(10) Patent No.: US PP13,899 P3
(45) Date of Patent: Jun. 24, 2003

(54) CHRYSANTHEMUM PLANT NAMED 'GEDI ONE MIS'

(75) Inventor: Dirk Pieters, Staden (BE)

(73) Assignee: Pieters Plant Production, Bvba, Oostnieuwkerke (BE)

( * ) Notice: Subject to any disclaimer, the term of this patent is extended or adjusted under 35 U.S.C. 154(b) by 20 days.

(21) Appl. No.: 09/873,905

(22) Filed: Jun. 4, 2001

(65) Prior Publication Data

US 2003/0005503 P1 Jan. 2, 2003

(51) Int. Cl.[7] ..... A01H 5/00
(52) U.S. Cl. ..... Plt./293

(58) Field of Search ..... Plt./293, 287, 290

(56) References Cited

U.S. PATENT DOCUMENTS

PP10,213 P 1/1998 Wain ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, and compact growth habit.

1 Drawing Sheet

LATIN NAME

*Dendranthema morifolium.*

VARIETY

Figure 1:
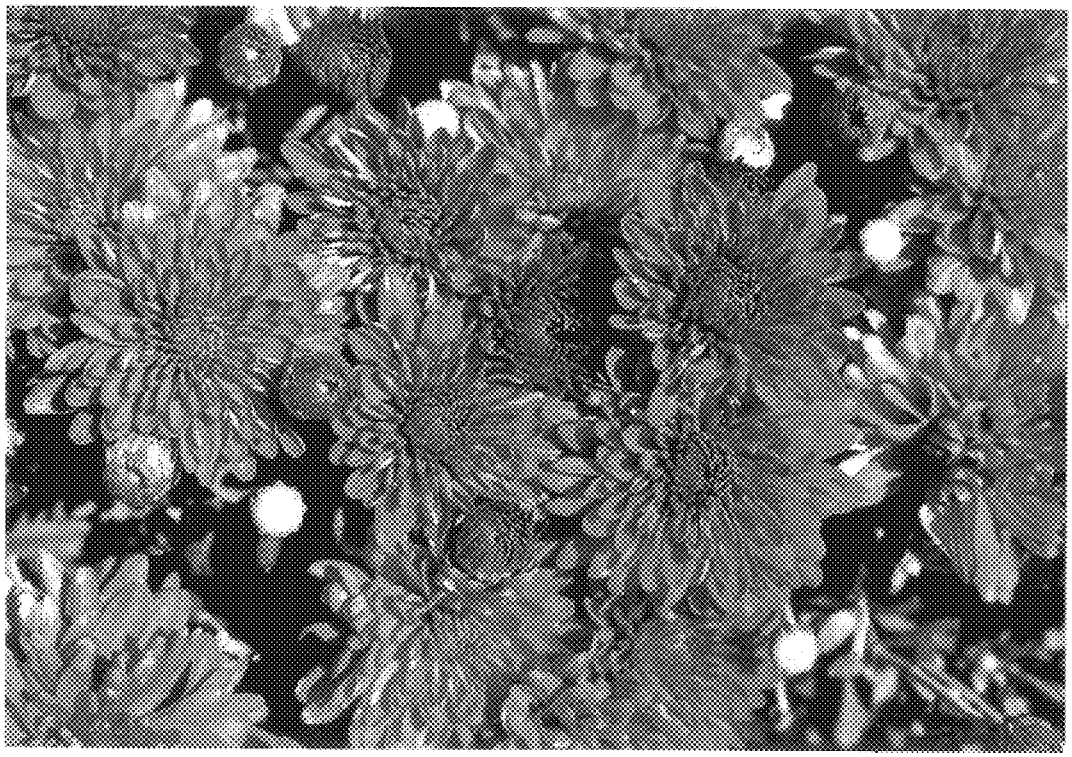

'GEDI ONE MIS'.

BACKGROUND OF THE INVENTION

The present invention relates to a new and distinct cultivar of Chrysanthemum plant, herein after referred to by the cultivar name 'GEDI ONE MIS'.

This new cultivar originated from hybridization of a female parent, cultivar 'Marenco' (unpatented in the United States), and a male parent cultivar 'Bronia' (unpatented in the United States). The new cultivar was discovered by the inventor in October 1996.

Asexual reproduction of the new cultivar by apical tip cutting and meristem tissue culture was performed in Oxnard, Calif and has shown that the unique features of this new cultivar are stable and reproduced true to type on successive generations.

SUMMARY OF THE INVENTION

The cultivar 'GEDI ONE MIS' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE MIS'. These characteristics in combination distinguish 'GEDI ONE MIS' as a new and distinct Chrysanthemum:

1. Decorative type inflorescence;
2. Consistent flowering response to short days, blooming consistently after 49 days of short day length;
3. Free branching habit; and
4. Compact growth habit.

Plants of the new cultivar are similar to plants of the parent cultivar, 'Marenco', in most horticultural characteristics, however plants of the new cultivar differed from plants of the cultivar 'Marenco' in the following characteristics:

1. The new cultivar naturally blooms 2 weeks earlier;
2. The new cultivar has blooms more uniformly;
3. The new cultivar has more blooms per flowering branch; and
4. The new cultivar has more ray florets.

Plants of the new cultivar are also similar to plants of the parent cultivar, 'Bronia,' in most horticultural characteristics, however plants of the new cultivar differed from plants of the cultivar 'Bronia ' in the following characteristics:

1. The new cultivar has different ray floret color;
2. The new cultivar has more blooms per flowering branch; and
3. The new cultivar has a wider diameter bloom.

The new cultivar can be compared to the Chrysanthemum cultivar 'Jenny Wren' (disclosed in U.S. Plant Pat. No. 10,213). However plants of the new Chrysanthemum differed from the plants of the cultivar 'Jenny Wren' in the following characteristics:

1. The new cultivar has more ray florets;
2. The new cultivar has a more round plant shape and greater branching;
3. The new cultivar has a shorter internode length;
4. The new cultivar has a more flexible plant form; and
5. The new cultivar has more blooms per flowering branch.

BRIEF DESCRIPTION OF THE PHOTOGRAPHS

The photograph shows a close up of the blooms, buds and leaves of 'GEDI ONE MIS'. Plants were grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types. The plant described was planted in mid-May from a rooted cutting, and was grown in a two-gallon container. The plant was pinched back 10 days after planting. The described plant was approximately 76 days old at the time of observation.

Botanical classification: *Dendranthema morifolium* cultivar 'GEDI ONE MIS'.
Commercial classification: Garden-type Chrysanthemum.
Parentage: Hybridization of female parent 'Marenco' (unpatented in the United States) and male parent 'Bronia' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 29 cm.
Growth rate: Moderate.
Plant spread: Approximately 31 cm.
Branching characteristics: Free Branching.
Length of lateral branches: Approximately 24 cm.
Number of leaves per lateral branch: Approximately 21.
Internode length: Approximately 2.2 cm.
Stem color: Near 137A.

FOLIAGE

Leaf:
- *Arrangement.*—Alternate, single.
- *Average length.*—Approximately 6.2 cm.
- *Average width.*—Approximately 3.7 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 138A. Young foliage under side: Near 138A. Mature foliage upper side: Near 137A. Mature foliage under side: Near 138A. Venation upper side: Near 137C. Venation under side: Near 137C.

Petiole:
- *Average length.*—Approximately 2.2 cm.
- *Average diameter.*—Approximately 0.4 cm.
- *Color.*—Approximately 137B.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately mid-September.
- *Number of inflorescences per stem.*—Approximately 11.
- *Inflorescence diameter.*—Approximately 7.2 cm.
- *Inflorescence depth.*—Approximately 2.2 cm.
- *Inflorescence longevity on plant.*—Approximately 22–26 days.
- *Persistence.*—Persistent.
- *Fragrance.*—Not present.

Ray florets:
- *Appearance.*—Matte.
- *Texture.*—Smooth.
- *Average number per inflorescence.*—Approximately 300.
- *Shape.*—Oblanceolate.
- *Margin.*—Entire.
- *Apex.*—Obtuse.
- *Width.*—Approximately 3.9 cm.
- *Width.*—Approximately 1.0 cm.
- *Color.*—Upper surface at first opening: Near 178A. Upper surface at maturity: Near 180A. Upper surface at fading: Near 180B. Under surface at first opening: Near 180A. Under surface at maturity: Near 180A. Under surface at fading: Near 180C.

Disc florets:
- *Appearance.*—Shiny.
- *Texture.*—Smooth.
- *Average number per inflorescence.*—Approximately 60.
- *Shape.*—Cylindric.
- *Apex.*—Obtuse.
- *Average length.*—Approximately 1.0 cm.
- *Average width.*—Approximately 0.2 cm.
- *Color.*—At first opening: Near 3D. At maturity: Near 16A. At fading: Near 16C.

Peduncle:
- *Length.*—At terminal end (shortest): Approximately 5 cm. At lateral end (longest): Approximately 8 cm.
- *Strength.*—Moderate.
- *Surface texture.*—Lightly pubescent.
- *Diameter.*—Aproximately 0.3 cm.
- *Color.*—Near 138B.
- *Habit.*—Erect.

Inflorescence bud:
- *Length.*—Approximately 1.0 cm.
- *Diameter.*—Approximately 1.0 cm.
- *Form.*—Globular.
- *Color.*—Near 178A.

Phyllaries:
- *Appearance.*—Matte.
- *Texture.*—Lightly pubescent.
- *Number.*—Approximately 30 to 40.
- *Shape.*—Ovate.
- *Margin.*—Entire.
- *Apex.*—Acute.
- *Diameter.*—Approximately 0.4 cm.
- *Length.*—Approximately 0.6 cm.
- *Color.*—Upper side: Near 137B. Under side: Near 137B.

REPRODUCTIVE ORGANS

Ray florets:

*Number of pistils per flower.*—1.
*Stigma shape.*—2 branched.
*Stigma color.*—Near 10B.
*Style color.*—Near 10D.
*Style length.*—Approximately 0.9 cm.
*Stamens.*—Absent.

Disc florets:

*Number of pistils per flower.*—1.
*Stigma shape.*—Cylindric.
*Style length.*—Approximately 0.5 cm.
*Number of stamens per flower.*—Approximately 5.
*Anther shape.*—Tubular.
*Anther color.*—Near 18A.
*Pollen color.*—Near 17C.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar. .

What is claimed is:

1. A new and distinct variety of Chrysanthemum plant named 'GEDI ONE MIS' as herein illustrated and described.

* * * * *